US012648852B2

(12) United States Patent
Smith et al.

(10) Patent No.: US 12,648,852 B2
(45) Date of Patent: Jun. 9, 2026

(54) PUMP AND VALVE SYSTEM FOR HYDRAULIC PRESSURIZATION OF IMPLANTS

(71) Applicant: Boston Scientific Scimed, Inc., Maple Grove, MN (US)

(72) Inventors: Noel Smith, County Kilkenny (IE); Daragh Nolan, County Waterford (IE); Thomas Andrew Albrecht, Edina, MN (US); Brian P. Watschke, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1347 days.

(21) Appl. No.: 16/738,667

(22) Filed: Jan. 9, 2020

(65) Prior Publication Data

US 2020/0222188 A1 Jul. 16, 2020

Related U.S. Application Data

(60) Provisional application No. 62/792,223, filed on Jan. 14, 2019.

(51) Int. Cl.
*A61F 2/26* (2006.01)
*A61F 2/00* (2006.01)
(Continued)

(52) U.S. Cl.
CPC .............. *A61F 2/26* (2013.01); *A61F 2/0027* (2013.01); *A61F 2/004* (2013.01); *A61M 39/223* (2013.01);
(Continued)

(58) Field of Classification Search
CPC .......... A61F 2/26; A61F 2/0027; A61F 2/484; A61F 2250/0013; A61F 2/004; A61F 2/12; A61M 39/223; A61M 39/24
See application file for complete search history.

(56) References Cited

U.S. PATENT DOCUMENTS 3,863,622 A * 2/1975 Buuck .................... A61F 2/004
128/DIG. 25
7,217,237 B2 5/2007 Schostek et al.
(Continued)

FOREIGN PATENT DOCUMENTS

EP 0202815 A2 11/1986
FR 2 878 733 A1 * 6/2006 ............... A61F 2/26
(Continued)

OTHER PUBLICATIONS

"Micro Dosing", Fraunhofer EMFT, retrieved from https://www.emft.fraunhofer.de/en/competences/micro-dosing.html, May 31, 2021, 4 pages.
(Continued)

*Primary Examiner* — David H Willse
(74) *Attorney, Agent, or Firm* — Brake Hughes Bellermann LLP

(57) ABSTRACT

According to an aspect, an implantable device includes a fluid reservoir configured to be implanted in a body of a patient at a first location, an inflatable member configured to be implanted in the body of the patient at a second location, and a pump assembly configured to be implanted in the body of the patient at a third location. The pump assembly is configured to transfer fluid from the fluid reservoir to the inflatable member in response to the implantable device being in an inflation mode, and the pump assembly configured to transfer the fluid from the inflatable member to the fluid reservoir in response to the implantable device being in a deflation mode. The pump assembly includes an electronic control module, an electronically powered pump, a first valve, and a second valve. The electronic control module is configured to activate or deactivate the electronically powered pump.

12 Claims, 7 Drawing Sheets

(51) Int. Cl.

| | |
|---|---|
| *A61F 2/48* | (2006.01) |
| *A61F 5/41* | (2006.01) |
| *A61M 39/22* | (2006.01) |
| *A61M 39/24* | (2006.01) |

(52) U.S. Cl.
CPC ............. *A61M 39/24* (2013.01); *A61F 2/484* (2021.08); *A61F 2005/415* (2013.01); *A61F 2250/0013* (2013.01)

(56) References Cited

U.S. PATENT DOCUMENTS

| | | | |
|---|---|---|---|
| 8,585,580 | B2 | 11/2013 | Kuyava et al. |
| 11,135,063 | B2 | 10/2021 | Weber et al. |
| 2004/0147886 | A1 | 7/2004 | Bonni |
| 2008/0214888 | A1* | 9/2008 | Ben Shalom ....... A61M 60/435 623/3.21 |
| 2011/0015738 | A1 | 1/2011 | Vaingast et al. |
| 2011/0202041 | A1 | 8/2011 | Forsell |
| 2018/0110623 | A1 | 4/2018 | Vaingast et al. |
| 2019/0350712 | A1 | 11/2019 | Weber et al. |

FOREIGN PATENT DOCUMENTS

| | | | |
|---|---|---|---|
| WO | 9204879 | A1 | 4/1992 |
| WO | 2015093681 | A1 | 6/2015 |
| WO | 2015200784 | A3 | 12/2015 |
| WO | 2019213236 | A1 | 11/2019 |

OTHER PUBLICATIONS

"Silicon Micro Diaphragm Pumps Portfolio", Fraunhofer EMFT, retrieved on Jun. 2, 2021 from https://www.emft.fraunhofer.de/content/dam/emft/en/documents/Infosheets/19_E_Micro_Diaphragm_pumps_portfolio_of_Fraunhofer_EMFT_public.pdf, 2 pages.

"The Smallest Micropump in the World", Fraunhofer EMFT, Press briefing, retrieved from https://www.emft.fraunhofer.de/en/mediacenter/press-briefings/2015-11-16_smallest-micropump.html, Nov. 16, 2015, 2 pages.

"Welling sensors uniquely positioned for Cardio-Vascular, urology and gastro-enterology applications", Welling, 3 pages.

Lewis, et al., "Blood Pressure Within the Corpus Cavernosum Penis of the Bull", J. Reprod. Fert. 17, 1968, pp. 155-156.

Scovell, et al., "Longitudinal and Horizontal Load Testing of Inflatable Penile Implant Cylinders of Two Manufacturers: An Ex Vivo Demonstration of Inflated Rigidity", J Sex Med. 13(11), Nov. 2016, 14 pages.

Wu, et al., "MEMS Flow Sensors for Nano-Fluidic Applications", Sensors and Actuators A 89, 2001, pp. 152-158.

International Search Report and Written Opinion for Application No. PCT/US2020/013114, mailed on Apr. 28, 2020, 12 pages.

First Office Action for Chinese Application No. 202080008141.1 (with English translation), mailed Jan. 31, 2024, 20 pages.

Extended European Search Report for European Application No. 25178507.7, mailed Aug. 11, 2025, 9 pages.

\* cited by examiner

500

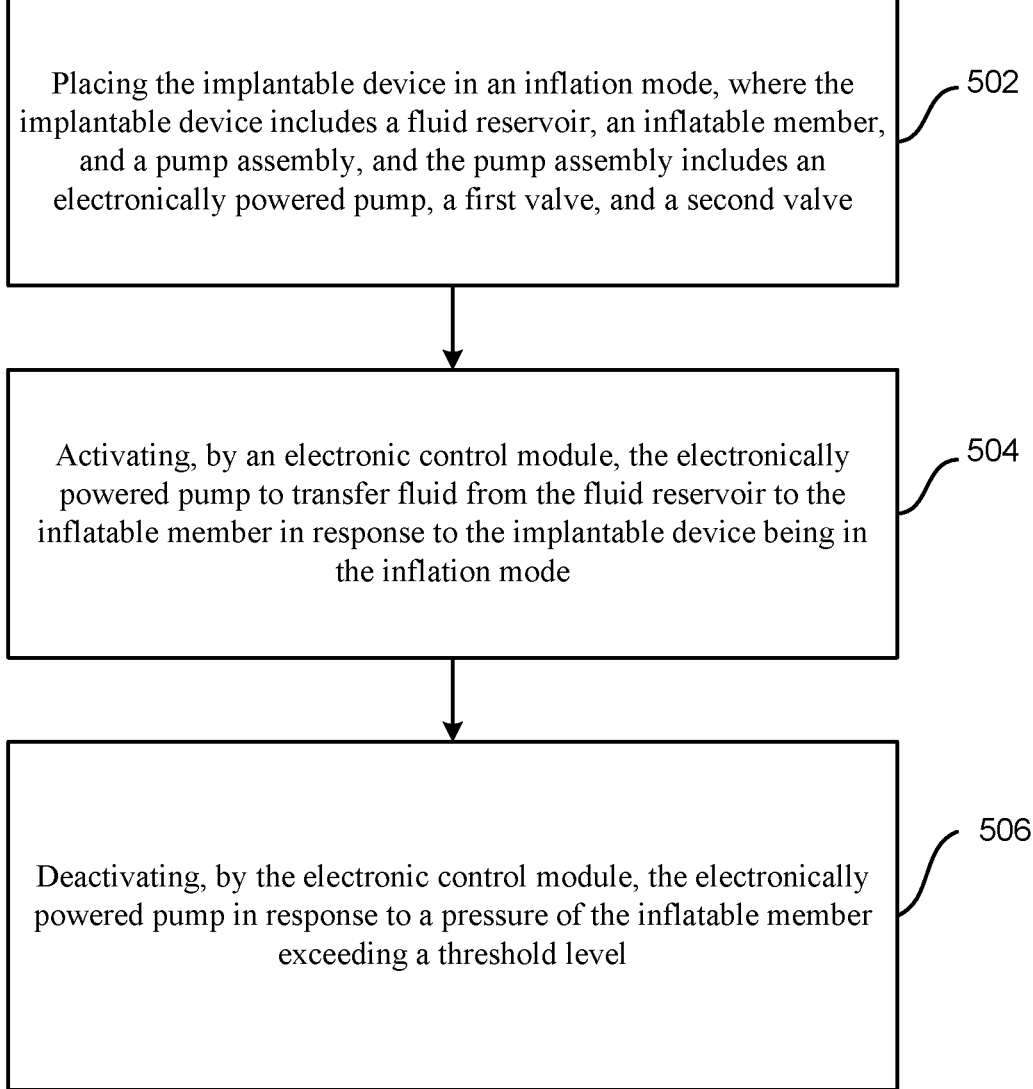

Placing the implantable device in an inflation mode, where the implantable device includes a fluid reservoir, an inflatable member, and a pump assembly, and the pump assembly includes an electronically powered pump, a first valve, and a second valve — 502

Activating, by an electronic control module, the electronically powered pump to transfer fluid from the fluid reservoir to the inflatable member in response to the implantable device being in the inflation mode — 504

Deactivating, by the electronic control module, the electronically powered pump in response to a pressure of the inflatable member exceeding a threshold level — 506

PUMP AND VALVE SYSTEM FOR HYDRAULIC PRESSURIZATION OF IMPLANTS

CROSS-REFERENCE TO RELATED APPLICATION

This application is a Nonprovisional of, and claims priority to, U.S. Patent Application No. 62/792,223, filed on Jan. 14, 2019, entitled "PUMP AND VALVE SYS TEM FOR HYDRAULIC PRESSURIZATION OF IMPLANTS", the disclosure of which is incorporated by reference herein in its entirety.

TECHNICAL FIELD

This disclosure relates generally to implantable devices having one or more electronically powered pumps and valves to move fluid between device components.

BACKGROUND

An implantable device such as a penile prosthesis or an artificial urinary sphincter device moves hydraulic fluid between various parts of the implantable device. In some examples, the implantable device includes a manual pump such as a fluid filled bulb and a set of valves to direct the fluid flow. To use the pump, the patient squeezes the bulb to generate pressure that drives fluid in the desired direction. The patient may also be required to press other buttons on the pumps to switch valve pathways to change pump valve pathways for different functions.

SUMMARY

According to an aspect, an implantable device includes a fluid reservoir configured to hold fluid, where the fluid reservoir is configured to be implanted in a body of a patient at a first location, an inflatable member configured to be implanted in the body of the patient at a second location, and a pump assembly configured to be implanted in the body of the patient at a third location. The pump assembly is configured to transfer the fluid from the fluid reservoir to the inflatable member in response to the implantable device being in an inflation mode, and the pump assembly configured to transfer the fluid from the inflatable member to the fluid reservoir in response to the implantable device being in a deflation mode. The pump assembly includes an electronic control module, an electronically powered pump, a first valve, and a second valve. The electronic control module is configured to activate or deactivate the electronically powered pump.

According to some aspects, the implantable device includes one or more of the following features (or any combination thereof). The implantable device includes a pressure sensor configured to monitor a pressure of the inflatable member. The pressure sensor is communicatively coupled to the electronic control module. The electronic control module is configured to deactivate the electronically powered pump in response to the pressure of the inflatable member exceeding a threshold level. The first valve may be an active valve configured to be electronically controlled. The first valve may be a passive one-way valve. The second valve may be an active valve configured to be electronically controlled. The second valve may be a passive one-way valve. The electronically powered pump may be a first electronically powered pump, and the pump assembly may include a second electronically powered pump, where the first valve is disposed in series with the first electronically powered pump, the second valve is disposed in series with the second electronically powered pump, and the second electronically powered pump is disposed in parallel with the first electronically powered pump. In some examples, the first electronically powered pump is activated and the second electronically powered pump is deactivated in response to the implantable device being in the inflation mode, and the first electronically powered pump is deactivated and the second electronically powered pump is activated in response to the implantable device being in the deflation mode. The first valve may include a three-way valve, and the second valve may include a three-way valve, and the electronically powered pump is disposed between the first valve and the second valve. The electronically powered pump may be a first electronically powered pump, and the pump assembly includes a second electronically powered pump and a third valve. The first electronically powered pump is configured to transfer the fluid from the fluid reservoir to the inflatable member in response to a pressure differential between the inflatable member and the fluid reservoir being less than a threshold amount, and the first electronically powered pump and the second electronically powered pump are configured to transfer the fluid from the fluid reservoir to the inflatable member in response to the pressure differential being greater than the threshold amount. The inflatable member may be a pair of inflatable cylinders configured to be implanted in a corpora cavernosa of the patient. The inflatable member may be an inflatable cuff configured to be placed around a urethra of the patient.

According to an aspect, an implantable device includes a fluid reservoir configured to hold fluid, where the fluid reservoir is configured to be implanted in a body of a patient at a first location, an inflatable member configured to be implanted in the body of the patient at a second location, and a pump assembly configured to be implanted in the body of the patient at a third location. The pump assembly is configured to transfer the fluid from the fluid reservoir to the inflatable member in response to the implantable device being in an inflation mode, and the pump assembly is configured to transfer the fluid from the inflatable member to the fluid reservoir in response to the implantable device being in a deflation mode. The pump assembly includes an electronic control module, an electronically powered pump, a first valve, a second valve, and an interface element. The electronic control module is configured to activate the electronically powered pump in response to activation of the interface element by the patient.

According to some aspects, the implantable device may include one or more of the above/below features (or any combination thereof). The implantable device may include a pressure sensor configured to monitor a pressure of the inflatable member, where the pressure sensor is communicatively coupled to the electronic control module, and the electronic control module is configured to deactivate the electronically powered pump in response to the pressure of the inflatable member exceeding a threshold level. The electronically powered pump may be a first electronically powered pump, and the pump assembly may include a second electronically powered pump. The first electronically powered pump may be disposed in parallel with the second electronically powered pump. The first electronically powered pump may be disposed in series with the second electronically powered pump.

According to an aspect, a method for transferring fluid in an implantable device includes placing the implantable device in an inflation mode, where the implantable device includes a fluid reservoir, an inflatable member, and a pump assembly, and the pump assembly includes an electronically powered pump, a first valve, and a second valve. The method includes activating, by an electronic control module, the electronically powered pump to transfer fluid from the fluid reservoir to the inflatable member in response to the implantable device being in the inflation mode, and deactivating, by the electronic control module, the electronically powered pump in response to a pressure of the inflatable member exceeding a threshold level. In some examples, the method includes controlling, by the electronic control module, the first valve and the second valve.

BRIEF DESCRIPTION OF THE DRAWINGS

FIG. 5 illustrates a flow chart depicting example operations of a method of transferring fluid in an implantable device according to an aspect.

DETAILED DESCRIPTION

Figure 1:
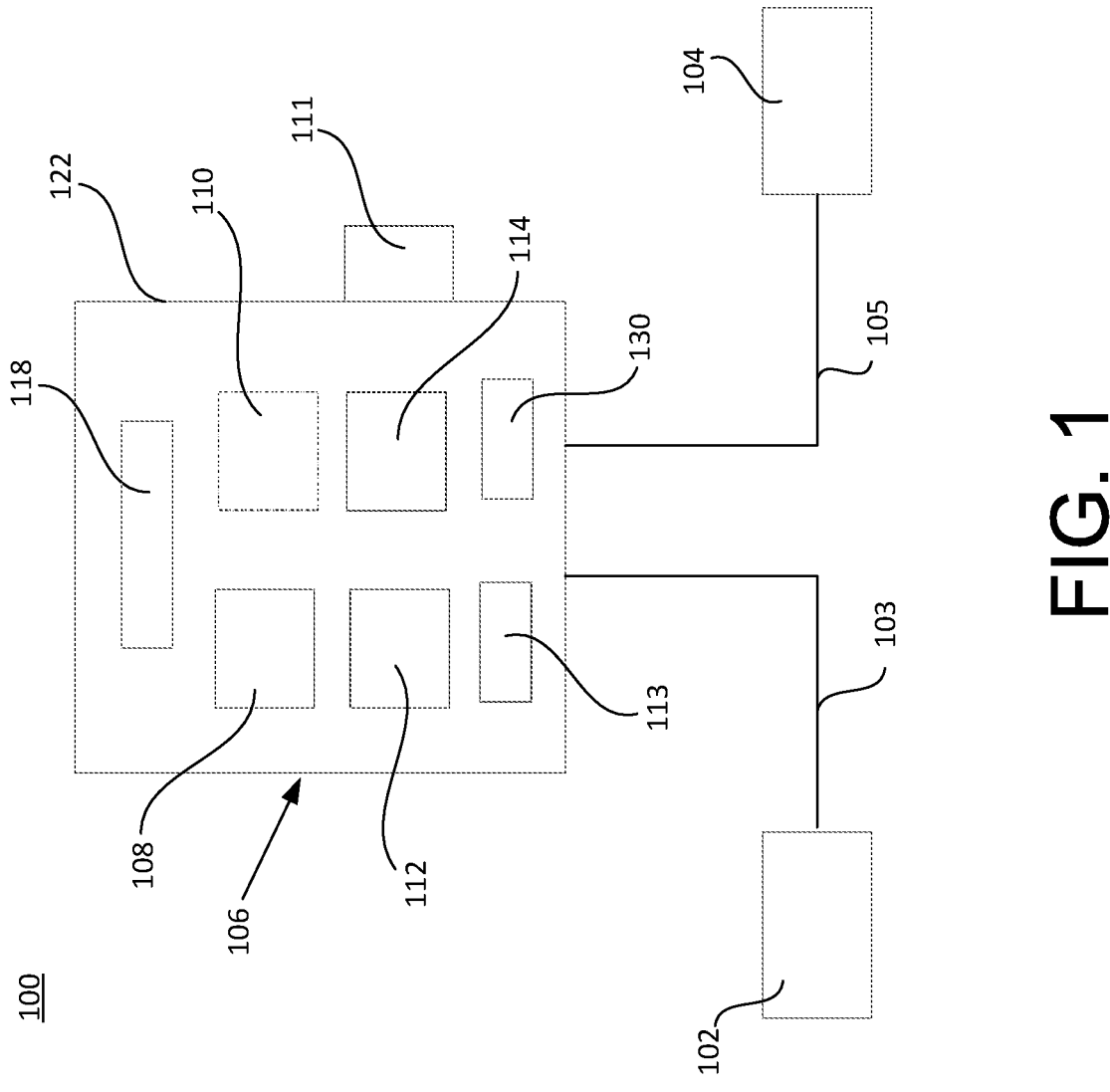
FIG. 1 illustrates an implantable device according to an aspect.

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the present disclosure.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "moveably coupled," as used herein, is defined as connected, although not necessarily directly and mechanically.

In general, the embodiments are directed to bodily implants. The term patient or user may hereafter be used for a person who benefits from the medical device or the methods disclosed in the present disclosure. For example, the patient can be a person whose body is implanted with the medical device or the method disclosed for operating the medical device by the present disclosure.

Manually manipulating the pump for these devices can be challenging for patients for a number of reasons. For example, it may be difficult to identify the different areas of the pump (e.g., deflate/lockout button, bulb, etc.) through the skin, especially for patients with diabetic neuropathy or those with poor dexterity for any number of reasons. Also, it may be difficult to learn how to use the device and several training sessions are often needed for patients to be able to successfully manipulate the pump. This may be exacerbated by the fact the pumps do not provide immediate positive feedback that they are being used correctly, and it may take a large amount of force to properly pressure the inflatable penile prosthesis, which may be difficult for older or arthritic patients to achieve. Exerting this much force on the pump through the skin can also cause contusions. Further, manually interacting with the pump reminds patients that they are using an implant and does not feel as natural as it might if the device were able to function without the patient interacting with the pump.

According to an aspect, the implantable device includes an electronically powered pump and a fluid circuit having a set of valves to move fluid instead of a manually powered pump. The fluid circuit allows fluid to be appropriately directed within the implant to achieve inflation, deflation, pressurization, depressurization, and deactivation of different fluid fill implant components without requiring the user to manually manipulate the pump or fluid circuit. In some examples, the pressure sensors or other sensors can be incorporated into the fluid circuit to allow for more nuanced control of pressure and volume transfer within the fluid circuit.

FIG. 1 illustrates an implantable device 100 according to an aspect. In some examples, the implantable device 100 is an inflatable penile prosthesis. In some examples, the implantable device 100 is an artificial urinary sphincter device. However, the implantable device 100 may include any type of medical device that transfers fluid between components of the implantable device 100.

The implantable device 100 includes a fluid reservoir 102, an inflatable member 104, and a pump assembly 106 configured to transfer fluid between the fluid reservoir 102 and the inflatable member 104. The fluid reservoir 102 is configured to be implanted in a body of a patient at a first location. In some examples, the first location is an abdomen of the patient. In some examples, the first location is a pelvic cavity of the patient. The inflatable member 104 is configured to be implanted in the body of the patient at a second location. In some examples, the second location is the corpus cavernosae of the patient. In some examples, the second location is around a urethra of the patient. The pump assembly 106 is configured to be implanted in the body of the patient at a third location. In some examples, the third location is the scrotum of the patient.

The fluid reservoir 102 may include a container having an internal chamber configured to hold or house fluid that is used to inflate the inflatable member 104. In some examples, the fluid reservoir 102 is a pressurized balloon. The volumetric capacity of the fluid reservoir 102 may vary depending on the size of the implantable device 100. In some examples, the volumetric capacity of the fluid reservoir 102 may be 3 to 150 cubic centimeters. In some examples, the fluid reservoir 102 is constructed from the same material as the inflatable member 104. In other examples, the fluid reservoir 102 is constructed from a different material than the inflatable member 104. In some examples, the fluid reservoir 102 contains a larger volume of fluid than the inflatable member 104.

In some examples, the inflatable member 104 is a pair of inflatable cylinders that are implanted into the corpus cavernosae of the patient, and the pump assembly 106 is configured to move fluid to pressure the inflatable cylinders to achieve an erection. When not in use, the cylinders are deflated and the system pressure returns to low ambient pressure. In some examples, the inflatable member 104 includes a first cylinder member and a second cylinder member. The volumetric capacity of the inflatable member 104 may depend on the size of the inflatable cylinders. In some examples, the volume of fluid in each cylinder may vary from about 10 milliliters in smaller cylinders and to about 50 milliliters in larger sizes. In some examples, the first cylinder member may be larger than the second cylinder member. In other examples, the first cylinder member may have the same size as the second cylinder member.

In some examples, the inflatable member 104 is an inflatable cuff that is implanted around the urethra, and the pump assembly 106 is configured to move fluid to pressure the inflatable cuff, which constricts the urethra, thereby restricting the flow of urine. To urinate, the patient may operate the pump assembly 106 to depressurize the inflatable cuff by transferring fluid from the inflatable cuff to the fluid reservoir 102.

The pump assembly 106 is coupled to the fluid reservoir 102 via a first conduit connector 103, and the pump assembly 106 is coupled to the inflatable member 104 via a second conduit connector 105. Each of the first conduit connector 103 and the second conduit connector 105 may define a lumen configured to transfer the fluid to and from the pump assembly 106. For example, the first conduit connector 103 may define a first lumen configured to transfer fluid between the pump assembly 106 and the fluid reservoir 102. The first conduit connector 103 may include a single or multiple tube members for transferring the fluid between the pump assembly 106 and the fluid reservoir 102. The second conduit connector 105 may define a second lumen configured to transfer fluid between the pump assembly 106 and the inflatable member 104. The second conduit connector 105 may include a single or multiple tube members for transferring the fluid between the pump assembly 106 and the inflatable member 104. In some examples, the first conduit connector 103 and the second conduit connector 105 may include a silicone rubber material. In some examples, the pump assembly 106 may be directly connected to the fluid reservoir 102.

The pump assembly 106 may include a valve body 122 that defines fluid passageways through the valve body 122. In some examples, the valve body 122 includes a block of material that defines the fluid passageways and encloses the valve/pump components. In some examples, the valve body 122 includes a silicone material. In some examples, the valve body 122 may be molded from a silicone material having a medium durometer value. In some examples, the pump assembly 106 includes an outer protective casing that is disposed over the valve body 122. In some examples, the outer protective casing has a material (e.g., a polymer material) that is different from the valve body 122. In some examples, the outer protective casing includes one or more tactile features that help the user locate the valve body 122. In some examples, the tactile features include protruded portions, ridges, grooves, bumps, and/or depressions.

The pump assembly 106 includes an electronically powered pump 108, a first valve 112, and a second valve 114 disposed within the fluid passageways of the valve body 122. The pump assembly 106 includes an electronic control module 113 and a battery 130. The battery 130 is configured to power the electronically powered pump 108, the first valve 112, the second valve 114, the electronic control module 113, and/or other components of the pump assembly 106. In some examples, the electronically powered pump 108 is a one-way pump. In some examples, the pump assembly 106 includes a third valve. In some examples, the pump assembly 106 includes a fourth valve. The valves of the pump assembly 106 may include passive one-way valves and/or active valves that are electronically controlled. In some examples, the pump assembly 106 includes a secondary electronically powered pump 110 disposed in a fluid passageway of the valve body 122.

The electronic control module 113 is configured to electronically activate and deactivate the electronically powered pump 108 and/or the secondary electronically powered pump 110. The electronically powered pump(s) are configured to transfer the fluid from the fluid reservoir 102 to the inflatable member 104 when the implantable device 100 is in an inflation mode, and transfer the fluid from the inflatable member 104 to the fluid reservoir 102 when the implantable device 100 is in a deflation mode. The valves are configured to control the flow of the fluid through the valve body 122 in the inflation mode and the deflation mode. In some examples, the electronic control module 113 is communicatively coupled to an interface element 111. In some examples, the interface element 111 is a component that is operated by a patient to inflate and/or deflate the inflatable member 104. In some examples, the interface element 111 includes a button, switch, or a push rod, or other patent interface element(s) that control operation(s) of the implantable device 100.

In some examples, the first valve 112 includes a passive one-way valve. In some examples, the passive one-way valve includes a duckbill valve. In some examples, the passive one-way valve includes a movable valve component (e.g., ball, poppet, etc.) and a biasing member (e.g., a spring). In some examples, the first valve 112 includes an active valve that is electronically activated by the electronic control module 113. In some examples, the first valve 112 includes an active three-way valve that is electronically controlled. In some examples, the first valve 112 includes a set of two parallel active valves. In some examples, the second valve 114 includes a passive one-way valve. In some examples, the second valve 114 includes an active valve that is electronically activated by the electronic control module 113. In some examples, the second valve 114 includes an active three-way valve that is electronically controlled. In some examples, the second valve 114 includes a set of two parallel active valves.

In some examples, the pump assembly 106 (or the implantable device 100) includes a pressure sensor 118 configured to monitor (or sense) a pressure of the inflatable member 104. The pressure sensor 118 is communicatively coupled to the electronic control module 113. The electronic control module 113 is configured to deactivate the electronically powered pump 108 and/or the secondary electronically powered pump 110 in response to the pressure of the inflatable member 104 exceeding a threshold level. In some examples, the pressure sensor 118 (or a separate pressure sensor) is configured to monitor (or sense) the pressure of the fluid reservoir 102, and the electronic control module 113 is configured to determine a pressure differential across the pump assembly 106 based on the sensed pressure of the fluid reservoir 102 and the sensed pressure of the inflatable member 104.

In some examples, the first valve 112 is disposed in series with the electronically powered pump 108, and the second valve 114 is disposed in series with the secondary electronically powered pump 110, where the secondary electronically powered pump 110 is disposed in parallel with the electronically powered pump 108. The first valve 112 and the second valve 114 may be passive one-way valves or active valves that are electronically opened and closed. In this example, the electronically powered pump 108 is activated and the secondary electronically powered pump 110 is deactivated in response to the implantable device 100 being in the inflation mode. For example, the electronically powered pump 108 may transfer fluid from the fluid reservoir 102, through the pump assembly 106 (via the first valve 112—which is open if electronically controlled), and to the inflatable member 104 in the inflation mode. In some examples, the electronically powered pump 108 is deactivated and the secondary electronically powered pump 110 is activated in response to the implantable device 100 being in the deflation mode. For example, the secondary electronically powered pump 110 may transfer fluid from the inflatable member 104, through the pump assembly 106 (via the second valve 114—which is open if electronically controlled), and to the fluid reservoir 102 in the deflation mode.

In some examples, the pump assembly 106 includes the electronically powered pump 108 but not the secondary electronically powered pump 110. For example, the electronically powered pump 108 may be disposed between the first valve 112 and the second valve 114, where the first valve 112 and the second valve 114 are both active three-way valves (or each includes a set of two parallel active valves). In some examples, the first valve 112 may have a first port fluidly coupled to the fluid reservoir 102, a second port fluidly coupled to an input of the electronically powered pump 108, and a third port fluidly coupled to the inflatable member 104. The second valve 114 may have a first port fluidly coupled to the fluid reservoir 102, a second port fluidly coupled to an output of the electronically powered pump 108, and a third port fluidly coupled to the inflatable member 104. In some examples, the first valve 112 may have only two ports open at a particular time, and the electronic control module 113 may control which of the ports are open and which port is closed. Similarly, the second valve 114 may have only two ports open at a particular time, and the electronic control module 113 may control which of the ports are open and which port is closed.

In some examples, in the inflation mode, the third port of the first valve 112 is closed (and its other two ports are open), and the first port of the second valve 114 is closed (and its other two ports are open). In some examples, in the deflation mode, the first port of the first valve 112 is closed (and its other two ports are open), and the third port of the second valve 114 is closed (and it other two ports are open). To hold a set pressure in the inflatable member 104, the electronically powered pump 108 is deactivated and the first valve 112 and the second valve 114 are set to open channels between the same two components.

Figure 2:
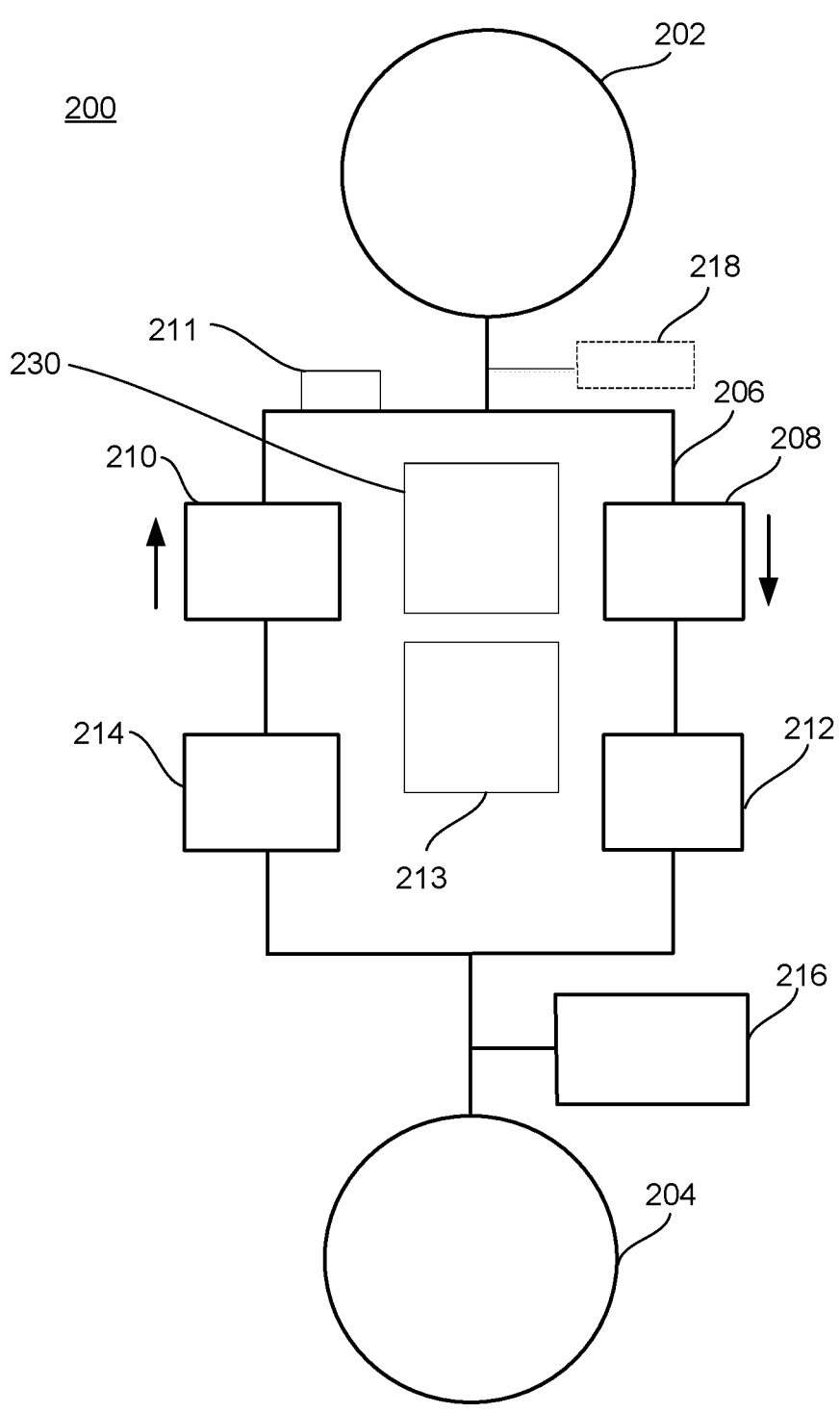
FIG. 2 illustrates an implantable device according to another aspect.

FIG. 2 illustrates an implantable device 200 according to an aspect. In some examples, the implantable device 200 is an inflatable penile prosthesis. In some examples, the implantable device 200 is an artificial urinary sphincter device. However, the implantable device 200 may include any type of medical device that transfers fluid between components of the implantable device 200.

The implantable device 200 includes a fluid reservoir 202, an inflatable member 204, and a pump assembly 206 configured to transfer fluid between the fluid reservoir 202 and the inflatable member 204 according to an aspect. In some examples, the fluid reservoir 202 may be implanted in the abdomen or pelvic cavity of the user (e.g., the fluid reservoir 202 may be implanted in the lower portion of the user's abdominal cavity or the upper portion of the user's pelvic cavity), and the pump assembly 206 may be implanted in the scrotum of the user.

In some examples, the inflatable member 204 is a pair of inflatable cylinders that are implanted into the corpus cavernosae of the patient, and the pump assembly 206 is configured to move fluid to pressure the inflatable cylinders to achieve an erection. When not in use, the cylinders are deflated and the system pressure returns to low ambient pressure. In some examples, the inflatable member 204 is an inflatable cuff that is implanted around a urethra, and the pump assembly 206 is configured to move fluid to pressure the inflatable cuff, which constricts the urethra, thereby restricting the flow of urine. To urinate, the patient operates the pump assembly 206 to depressurize the inflatable cuff by removing fluid.

The pump assembly 206 includes a first electronically powered pump 208, a second electronically powered pump 210, a first valve 212, a second valve 214, and an electronic control module 213. The pump assembly 206 may include a battery 230 configured to power the first electronically powered pump 208, the second electronically powered pump 210, the first valve 212, the second valve 214, and/or the electronic control module 213.

The first electronically powered pump 208 and the second electronically powered pump 210 are disposed in parallel with each other. The first valve 212 is coupled in series with the first electronically powered pump 208. The second valve 214 is coupled in series with the second electronically powered pump 210. For example, the first electronically powered pump 208 is fluidly connected to fluid reservoir 202 and the first valve 212. The first valve 212 is fluidly coupled to the first electronically powered pump 208 and the inflatable member 204. In some examples, the first electronically powered pump 208 is a one-way pump configured to transfer fluid from the fluid reservoir 202 to the inflatable member 204 during the inflation mode. The second electronically powered pump 210 is fluidly connected to the fluid reservoir 202 and the second valve 214. The second valve 214 is fluidly connected to the second electronically powered pump 210 and the inflatable member 204. The second electronically powered pump 210 is a one-way pump configured to transfer fluid from the inflatable member 204 to the fluid reservoir 202 during the deflation mode.

In some examples, the first valve 212 is an active valve that is electronically closed and opened, and the second valve 214 is an active valve that is electronically closed and opened. The active valve may be an electro-mechanical valve that is in either an open state (thereby allowing fluid to pass through) or a closed state (thereby blocking the passage of fluid). In some examples, the active valve may transition between the open state and the closed state based on a signal. In some examples, the active valve is an active latching valve that can be opened or closed electronically and stay in the open/closed state after switching even when power is not applied.

In some examples, the first valve 212 is a passive one-way valve, and the second valve 214 is a passive one-way valve. In some examples, the passive one-way valve includes a duckbill valve. In some examples, the passive one-way valve includes a movable valve component (e.g., ball, poppet, etc.) and a biasing member (e.g., spring). When the first valve 212 is the passive one-way valve, the first valve 212 may allow fluid to be transferred in the fluid direction of the first electronically powered pump 208 that is wired in series. When the second valve 214 is the passive one-way valve, the second valve 214 may allow fluid to be transferred in the fluid direction of the second electronically powered pump 210 that is wired in series.

The electronic control module 213 is configured to control the first electronically powered pump 208, the second electronically powered pump 210, the first valve 212, and/or the second valve 214. The electronic control module 213 may include one or more processors (e.g., coupled to a substrate) and a non-transitory computer readable medium that stores instructions executable by processors. In some examples, the electronic control module 213 is communicatively coupled to an interface element 211. In some examples, the interface element 211 is a component that is operated by a patient to inflate and/or deflate the inflatable member 204. In some examples, the interface element 211 includes a button, switch, or a push rod, or other patient interface element(s) that are configured to control operation(s) of the implantable device 100.

To inflate the inflatable member 204, the first electronically powered pump 208 is activated (e.g., turned-on) to move fluid from the fluid reservoir 202 to the inflatable member 204. For example, the patient may activate the interface element 211 to place the pump assembly 206 in the inflation mode, which causes the electronic control module 213 to activate the first electronically powered pump 208 (e.g., by sending a signal to the first electronically powered pump 208). In some examples, if the first valve 212 is an active valve, the electronic control module 213 is configured to open the first valve 212 (e.g., by sending a signal to the first valve 212).

To deflate the inflatable member 204, the second electronically powered pump 210 is activated to move fluid from the inflatable member 204 to the fluid reservoir 202. For example, the patient may activate the interface element 211 to place the pump assembly 206 in the deflation mode, which causes the electronic control module 213 to activate the second electronically powered pump 210 (e.g., by sending a signal to the second electronically powered pump 210). In some examples, if the second valve 214 is an active valve, the electronic control module 213 is configured to open the second valve 214 (e.g., by sending a signal to the second valve 214). To hold a set pressure in the inflatable member 204, the first electronically powered pump 208 and the second electronically powered pump 210 are deactivated (e.g., turned off) and the first valve 212 and the second valve 214 are closed if they are actively controlled valves.

The fluid reservoir 202 may include a container having an internal chamber configured to hold or house fluid that is used to inflate the inflatable member 204. In some examples, the fluid reservoir 202 is an unpressurized reservoir. In some examples, the fluid reservoir 202 is a pressured reservoir such as a pressure regulating balloon.

In some examples, the implantable device 200 or the pump assembly 206 includes a first pressure sensor 216 configured to monitor a pressure of the inflatable member 204. In some examples, the first pressure sensor 216 is communicatively coupled to the electronic control module 213. The first pressure sensor 216 may be configured to transmit pressure data (e.g., periodically or continuously) to the electronic control module 213, where the pressure data represents a current pressure of the inflatable member 204. The electronic control module 213 is configured to deactivate the first electronically powered pump 208 in response to the pressure of the inflatable member 204 reaching or exceeding a set pressure target. In some example, when the pump assembly 206 is in the deflation mode, the electronic control module 213 is configured to deactivate the second electronically powered pump 210 in response to the pressure of the inflatable member 204 being equal to or below a pressure threshold.

In some examples, the implantable device 200 or the pump assembly 206 includes a second pressure sensor 218 configured to monitor a pressure of the fluid reservoir 202, and transmit pressure data to the electronic control module 213, where the pressure data represents a current pressure of the fluid reservoir 202. In some examples, the electronic control module 213 receives the pressure data from the first pressure sensor 216 and the pressure data from the second pressure sensor 218, and determines the pressure differential across the pump assembly 206. The electronic control module 213 may be configured to deactivate the first electronically powered pump 208 and/or the second electronically powered pump 210 based on the pressure differential (e.g., the pressure differential being greater or less than a threshold level).

Figure 3:
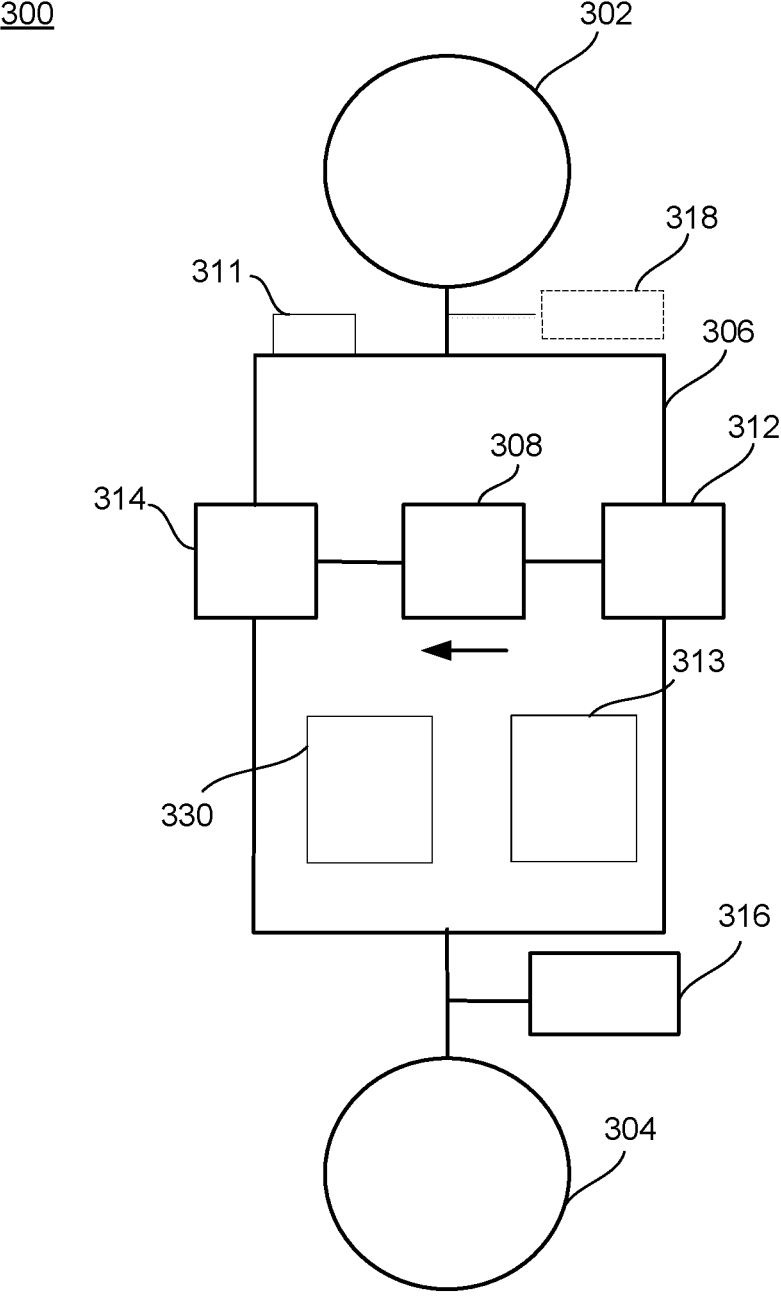
FIG. 3 illustrates an implantable device according to another aspect.

FIG. 3 illustrates an implantable device 300 according to an aspect. In some examples, the implantable device 300 is an inflatable penile prosthesis. In some examples, the implantable device 300 is an artificial urinary sphincter device. However, the implantable device 300 may include any type of medical device that transfers fluid between components of the implantable device 300.

The implantable device 300 includes a fluid reservoir 302, an inflatable member 304, and a pump assembly 306 configured to transfer fluid between the fluid reservoir 302 and the inflatable member 304. In some examples, the fluid reservoir 302 may be implanted in the abdomen or pelvic cavity of the user (e.g., the fluid reservoir 302 may be implanted in the lower portion of the user's abdominal cavity or the upper portion of the user's pelvic cavity), and the pump assembly 306 may be implanted in the scrotum of the user.

In some examples, the inflatable member 304 is a pair of inflatable cylinders that are implanted into the corpus cavernosae of the patient, and the pump assembly 306 is configured to move fluid to pressure the inflatable cylinders to achieve an erection. When not in use, the cylinders are deflated and the system pressure returns to low ambient pressure. In some examples, the inflatable member 304 is an inflatable cuff that is implanted around a urethra, and the pump assembly 306 is configured to move fluid to pressure the inflatable cuff, which constricts the urethra, thereby restricting the flow of urine. To urinate, the patient operates the pump assembly 306 to depressurize the inflatable cuff by removing fluid.

The pump assembly 306 includes an electronically powered pump 308, a first valve 312, a second valve 314, and an electronic control module 313. The pump assembly 306 may include a battery 330 configured to power the electronically powered pump 308, the first valve 312, the second valve 314, and/or the electronic control module 313. The electronically powered pump 308 is disposed between the first valve 312 and the second valve 314. In some examples, each of the first valve 312 and the second valve 314 is a three-way valve that is electronically controlled (e.g., only one of the three ports can be closed at a time). In some examples, each of the first valve 312 and the second valve 314 may be an active three-way valve that is electronically switched between a first state in which one of the three ports is closed and a second state in which a different one of the three ports is closed. In some examples, the first valve 312 is not a three-way active valve, but a set of two parallel active simple valves (e.g., a first active valve in parallel with a second active valve). In some examples, the second valve 314 is not a three-way active valve, but a set of two parallel active simple valves (e.g., a first active valve in parallel with a second active valve).

The first valve 312 includes a first port fluidly connected to the fluid reservoir 302, a second port fluidly connected to an input of the electronically powered pump 308, and a third port fluidly connected to the inflatable member 304. One of the first port, the second port, and the third port of the first valve 312 are closed at a particular time. The first valve 312 is configured to be activated between a first state in which only one of its first, second, and third ports are closed (other two are open), and a second state in which a different one of its first, second, and third ports are closed (other two are open). The second valve 314 includes a first port fluidly connected to the fluid reservoir 302, a second port fluidly connected to an output of the electronically powered pump 308, and a third port fluidly connected to the inflatable member 304. One of the first port, the second port, and the third port of the second valve 314 are closed at a particular time. The second valve 314 is configured to be activated between a first state in which only one of its first, second, and third ports are closed (other two are open), and a second state in which a different one of its first, second, and third ports are closed (other two are open).

The electronic control module 313 is configured to control the electronically powered pump 308, the first valve 312, and/or the second valve 314. The electronic control module 313 may include one or more processors (e.g., coupled to a substrate) and a non-transitory computer readable medium that stores instructions executable by processors. In some examples, the electronic control module 313 is communicatively coupled to an interface element 311. In some examples, the interface element 311 is a component that is operated by a patient to inflate and/or deflate the inflatable member 304. In some examples, the interface element 311 includes a button, switch, or a push rod, or other patent interface element(s) that control operation(s) of the implantable device 300.

In order to inflate the inflatable member 304, the first valve 312 is activated to the first state in which the first port and the second port are open and the third port is closed, thereby opening the channels to the fluid reservoir 302 and the input to the electronically powered pump 308, and the second valve 314 is activated to the first state in which the second port and the third port are open and the first port is closed, thereby opening the channels to the inflatable member 304 and the output of the electronically powered pump 308. The electronically powered pump 308 is activated to move the fluid from the fluid reservoir 302 to the inflatable member 304. For example, the patient may activate the interface element 311 to place the pump assembly 306 in the inflation mode, which causes the electronic control module 313 to activate the first valve 312 to the first state, activate the second valve 314 to the first state, and activate the electronically powered pump 308.

In order to deflate the inflatable member 304, the first valve 312 is activated to a second state in which the second port and the third port are open and the first port is closed, thereby opening the channels to the inflatable member 304 and the input to the electronically powered pump 308, and the second valve 314 is activated to a second state in which the first port and the second port is open and the third port is closed, thereby opening the channels to the fluid reservoir 302 and the output of the electronically powered pump 308. The electronically powered pump 308 is activated to move fluid from the inflatable member 304 to the fluid reservoir 302. For example, the patient may activate the interface element 311 to place the pump assembly 306 in the deflation mode, which causes the electronic control module 313 to activate the first valve 312 to the second state, activate the second valve 314 to the second state, and activate the electronically powered pump 308.

To hold a set pressure in the inflatable member 304, the electronically powered pump 308 is deactivated and the first valve 312 and the second valve 314 are set to open channels between the same two components. For example, the first and second ports of the first valve 312 are set to open (the third port being set to close) and the first and second ports of the second valve 314 are set to open (the third port being set to close), or the second and third ports of the first valve 312 are set to open (the first port being set to close) and the second and third ports of the second valve 314 are set to open (the first port being set to close).

The fluid reservoir 302 may include a container having an internal chamber configured to hold or house fluid that is used to inflate the inflatable member 304. In some examples, the fluid reservoir 302 is an unpressurized reservoir. In some examples, the fluid reservoir 302 is a pressured reservoir such as a pressure regulating balloon.

In some examples, the implantable device 300 or the pump assembly 306 includes a first pressure sensor 316 configured to monitor a pressure of the inflatable member 304. In some examples, the first pressure sensor 316 is communicatively coupled to the electronic control module 313. The first pressure sensor 316 may be configured to transmit pressure data to the electronic control module 313, where the pressure data represents a current pressure of the inflatable member 304. The electronic control module 313 is configured to deactivate the electronically powered pump 308 in response to the pressure of the inflatable member 304 reaching or exceeding a set pressure target. In some examples, when the pump assembly 306 is in the deflation mode, the electronic control module 313 is configured to deactivate the electronically powered pump 308 in response to the pressure of the inflatable member 304 being equal to or below a pressure threshold.

In some examples, the implantable device 300 or the pump assembly 306 includes a second pressure sensor 318 configured to monitor a pressure of the fluid reservoir 302, and transmit pressure data to the electronic control module 313, where the pressure data represents a current pressure of the fluid reservoir 302. In some examples, the electronic control module 313 receives the pressure data from the first pressure sensor 316 and the pressure data from the second pressure sensor 318, and determines the pressure differential across the pump assembly 306. The electronic control module 313 may be configured to deactivate the electronically powered pump 308 based on the pressure differential.

Figure 4:
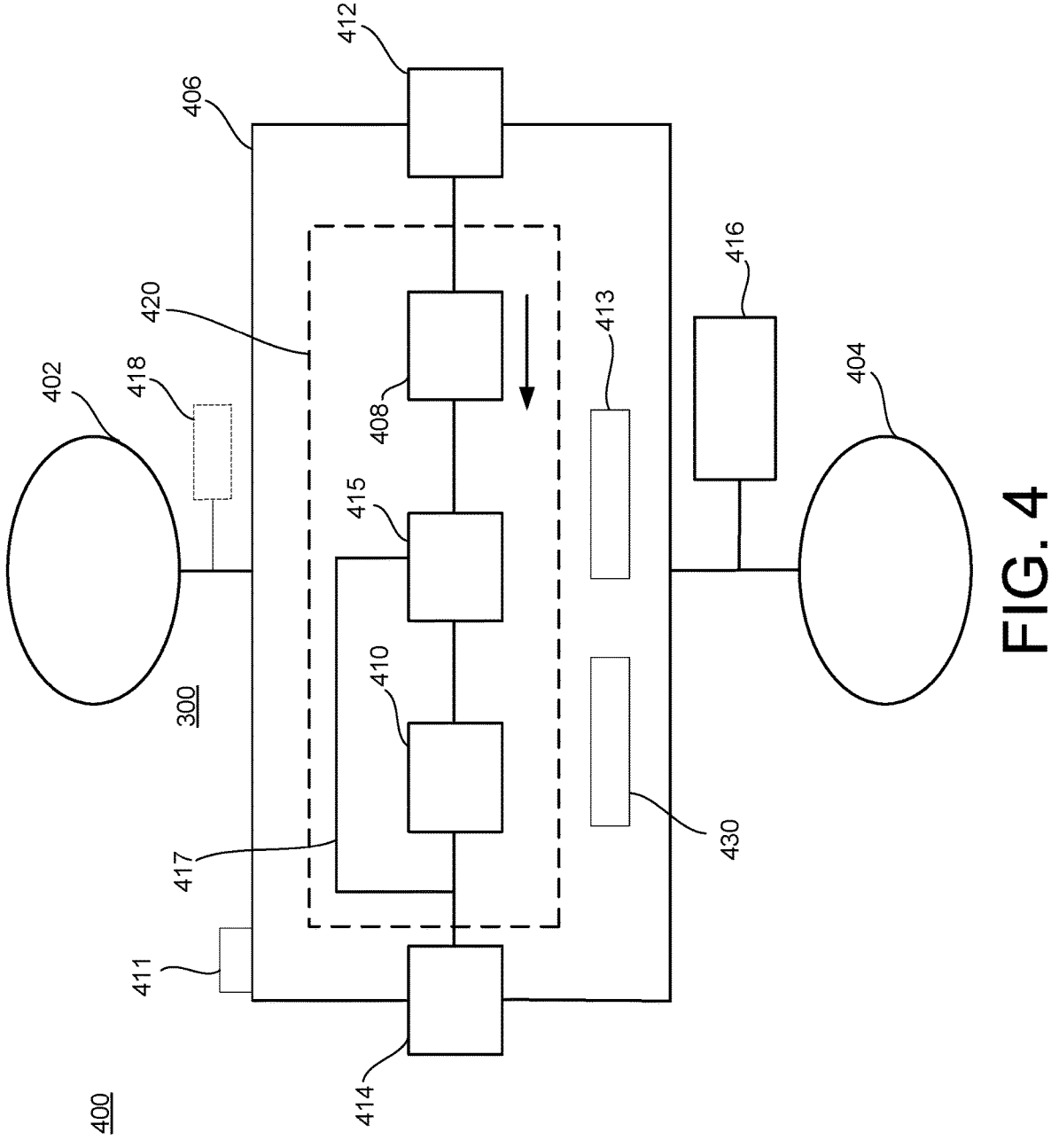
FIG. 4 illustrates an implantable device according to another aspect.

FIG. 4 illustrates an implantable device 400 according to an aspect. In some examples, the implantable device 400 is an inflatable penile prosthesis. In some examples, the implantable device 400 is an artificial urinary sphincter device. However, the implantable device 400 may include any type of medical device that transfers fluid between components of the implantable device 400.

The implantable device 400 includes a fluid reservoir 402, an inflatable member 404, and a pump assembly 406 configured to transfer fluid between the fluid reservoir 402 and the inflatable member 404. In some examples, the fluid reservoir 402 may be implanted in the abdomen or pelvic cavity of the user (e.g., the fluid reservoir 402 may be implanted in the lower portion of the user's abdominal cavity or the upper portion of the user's pelvic cavity), and the pump assembly 406 may be implanted in the scrotum of the user.

In some examples, the inflatable member 404 is a pair of inflatable cylinders that are implanted into the corpus cavernosae of the patient, and the pump assembly 406 is configured to move fluid to pressure the inflatable cylinders to achieve an erection. When not in use, the cylinders are deflated and the system pressure returns to low ambient pressure. In some examples, the inflatable member 404 is an inflatable cuff that is implanted around a urethra, and the pump assembly 406 is configured to move fluid to pressure the inflatable cuff, which constricts the urethra, thereby restricting the flow of urine. To urinate, the patient operates the pump assembly 406 to depressurize the inflatable cuff by removing fluid.

The pump assembly 406 includes a first valve 412, a second valve 414, an electronic control module 413, and a two-stage pump block 420 having a first electronically powered pump 408, a second electronically powered pump 410, and a third valve 415. The pump assembly 406 may include a battery 430 configured to power the first valve 412, the second valve 414, the electronic control module 413, and/or the two-stage pump block 420. The two-stage pump block 420 is disposed between the first valve 412 and the second valve 414. In some examples, the pump assembly 406 includes the same fluid circuit as the pump assembly 306 of FIG. 3 in order to inflate and deflate the inflatable member 404 except that a single pump is replaced by the two-stage pump block 420 in order to achieve higher pressures.

In some examples, each of the first valve 412 and the second valve 414 may be an active three-way valve that is electronically controlled between a first state in which one of the three ports is closed and a second state in which a different one of the three ports is closed. For example, in either of the first state or the second state, only one of the three ports is closed (with the other two being opened). In some examples, the first valve 412 is not a three-way active valve, but a set of two parallel active simple valves (e.g., a first active valve in parallel with a second active valve). In some examples, the second valve 414 is not a three-way active valve, but a set of two parallel active simple valves (e.g., a first active valve in parallel with a second active valve).

The first valve 412 includes a first port fluidly connected to the fluid reservoir 402, a second port fluidly connected to an input of the two-stage pump block 420, and a third port fluidly connected to the inflatable member 404. The second valve 414 includes a first port fluidly connected to the fluid reservoir 402, a second port fluidly connected to an output of the two-stage pump block 420, and a third port fluidly connected to the inflatable member 404. The first valve 412 is configured to be activated between a first state in which only one of the first, second, and third ports are closed (other two are open), and a second state in which a different one of the first, second, and third ports are closed (other two are open), and the second valve 414 is configured to be activated between a first state in which only one of the first, second, and third ports are closed (other two are open), and a second state in which a different one of the first, second, and third ports are closed (other two are open).

The two-stage pump block 420 includes two pumps in series, e.g., the first electronically powered pump 408 and the second electronically powered pump 410 are disposed in series. In some examples, the first electronically powered pump 408 and the second electronically powered pump 410 are disposed in parallel to each other to allow independent operation from each other (e.g., with the second electronically powered pump 410 taking over once the output pressure is too high for the first electronically powered pump 408). The third valve 415 is disposed between the first electronically powered pump 408 and the second electronically powered pump 410. In some examples, the third valve 415 is an active three-way valve that is electronically switched between a first state in which one of the three ports is closed and a second state in which a different one of the three ports is closed. In some examples, the third valve 415 is not a three-way valve, but a set of two parallel active valves. The third valve 415 includes a first port fluidly connected to an output of the first electronically powered pump 408, a second port fluidly connected to a bypass channel 417 that is fluidly connected to the second valve 414 (e.g., the bypass channel 417 bypasses the second electronically powered pump 410), and a third port fluidly connected to an input of the second electronically powered pump 410.

The first electronically powered pump 408 is a one-way pump. In some examples, the first electronically powered pump 408 is configured to pump fluid according to a first pressure and a first flow rate. The second electronically powered pump 410 is a one-way pump. In some examples, the second electronically powered pump 410 is configured to pump fluid according to a second pressure and a second flow rate. In some examples, the first pressure is less than the second pressure, and the first flow rate is higher than second flow rate. In some examples, the first electronically powered pump 408 is a low pressure, high flow rate pump, and the second electronically powered pump 410 is a high pressure, low flow rate pump.

The electronic control module 413 is configured to control the first electronically powered pump 408, the second electronically powered pump 410, the first valve 412, the second valve 414, and the third valve 415. The electronic control module 413 may include one or more processors (e.g., coupled to a substrate) and a non-transitory computer readable medium that stores instructions executable by processors. In some examples, the electronic control module 413 is communicatively coupled to an interface element 411. In some examples, the interface element 411 is a component that is operated by a patient to inflate and/or deflate the inflatable member 404. In some examples, the interface element 411 includes a button, switch, or a push rod, or other patient interface element(s) that control operation(s) of the implantable device 400.

In order to inflate the inflatable member 404, the first valve 412 is activated to the first state in which the first port and the second port are open and the third port is closed, thereby opening the channels to the fluid reservoir 402 and the input to the two-stage pump block 420, and the second valve 414 is activated to the first state in which the second port and the third port are open and the first port is closed, thereby opening the channels to the inflatable member 404 and the output of the two-stage pump block 420. In some examples, the two-stage pump block 420 is initially activated in a first state to move the fluid from the fluid reservoir 402 to the inflatable member 404. For example, the patient may activate the interface element 411 to place the pump assembly 406 in the inflation mode, which causes the electronic control module 413 to activate the first valve 412 to the first state, activate the second valve 414 to the first state, and activate the two-stage pump block 420 to the first state.

When the two-stage pump block 420 is in the first state, the first electronically powered pump 408 is activated, and the second electronically powered pump 410 is deactivated. For example, the third valve 415 is activated to a first state in which its first port and second port are open (and the third port is closed), thereby opening the channels to the output of the first electronically powered pump 408 and the bypass channel 417. The inflatable member 404 is inflated using the first electronically powered pump 408 until the differential pressure between the inflatable member 404 and the fluid reservoir 402 becomes too high for the first electronically powered pump 408 to overcome. At this point, the two-stage pump block 420 is activated to a second state in which both the first electronically powered pump 408 and the second electronically powered pump 410 are activated. In the second state, the third valve 415 is activated to a second state in which the first port and the third port are open (and the second port is closed), thereby opening the channels to the output of the first electronically powered pump 408 and the input to the second electronically powered pump 410.

In order to deflate the inflatable member 404, the first valve 412 is activated to a second state in which the second port and the third port are open and the first port is closed, thereby opening the channels to the inflatable member 404 and the input to the two-stage pump block 420, and the second valve 414 is activated to a second state in which the first port and the second port is open and the third port is closed, thereby opening the channels to the fluid reservoir 402 and the output of the two-stage pump block 420. In the deflation mode, the two-stage pump block 420 may be activated to the first state (in which the first electronically powered pump 408 is activated and the second electronically powered pump 410 is deactivated) or the second state (in which both the first electronically powered pump 408 and the second electronically powered pump 410 are activated) in order to move fluid from the inflatable member 404 to the fluid reservoir 402. For example, the patient may activate the interface element 411 to place the pump assembly 406 in the deflation mode, which causes the electronic control module 413 to activate the first valve 412 to the second state, activate the second valve 414 to the second state, and activate the two-stage pump block 420 to either the first state or the second state.

To hold a set pressure in the inflatable member 404, the two-stage pump block 420 is deactivated (e.g., both the first electronically powered pump 408 and the second electronically powered pump 410 are deactivated), and the first valve 412 and the second valve 414 are set to open channels between the same two components. For example, the first and second ports of the first valve 412 are set to open (the third port being set to close) and the first and second ports of the second valve 414 are set to open (the third port being set to close), or the second and third ports of the first valve 412 are set to open (the first port being set to close) and the second and third ports of the second valve 414 are set to open (the first port being set to close).

The fluid reservoir 402 may include a container having an internal chamber configured to hold or house fluid that is used to inflate the inflatable member 404. In some examples, the fluid reservoir 402 is an unpressurized reservoir. In some examples, the fluid reservoir 402 is a pressured reservoir such as a pressure regulating balloon.

In some examples, the pump assembly 406 includes a first pressure sensor 416 configured to monitor a pressure of the inflatable member 404. In some examples, the first pressure sensor 416 is communicatively coupled to the electronic control module 413. The first pressure sensor 416 may be configured to transmit pressure data to the electronic control module 413, where the pressure data represents a current pressure of the inflatable member 404. The electronic control module 413 is configured to deactivate the first electronically powered pump 408 and/or the second electronically powered pump 410 in response to the pressure of the inflatable member 404 reaching or exceeding a set pressure target. In some examples, when the pump assembly 406 is in the deflation mode, the electronic control module 413 is configured to deactivate the first electronically powered pump 408 and/or the second electronically powered pump 410 in response to the pressure of the inflatable member 404 being equal to or below a pressure threshold.

In some examples, the pump assembly 406 includes a second pressure sensor 418 configured to monitor a pressure of the fluid reservoir 402, and transmit pressure data to the electronic control module 413, where the pressure data represents a current pressure of the fluid reservoir 402. In some examples, the electronic control module 413 receives the pressure data from the first pressure sensor 416 and the pressure data from the second pressure sensor 418, and determines the pressure differential across the pump assembly 406. In some examples, the electronic control module 413 may be configured to place the two-stage pump block 420 in the second state (e.g., both the first electronically powered pump 408 and the second electronically powered pump 410 being activated) based on the pressure differential. In some examples, the electronic control module 413 may be configured to deactivate the first electronically powered pump 408 and the second electronically powered pump 410 based on the pressure differential.

FIG. 5 illustrates a flow chart 500 depicting example operations of a method of transferring fluid in an implantable device according to an aspect. Although the flow chart 500 is explained with reference to the implantable device 100 of FIG. 1, the example operations of the flow chart 500 may be performed by any of the devices discussed herein.

Operation 502 includes placing the implantable device 100 in an inflation mode, where the implantable device 100 including the fluid reservoir 102, the inflatable member 104, and the pump assembly 106, and the pump assembly 106 includes the electronically powered pump 108, the first valve 112, and the second valve 114.

Operation 504 includes activating, by the electronic control module 113, the electronically powered pump 108 to transfer fluid from the fluid reservoir 102 to the inflatable member 104 in response to the implantable device being in the inflation mode.

Operation 506 includes deactivating, by the electronic control module 113, the electronically powered pump 108 in response to a pressure of the inflatable member 104 exceeding a threshold level. In some examples, the operations include controlling, by the electronic control module 113, the first valve 112 and the second valve 114.

Figure 6:
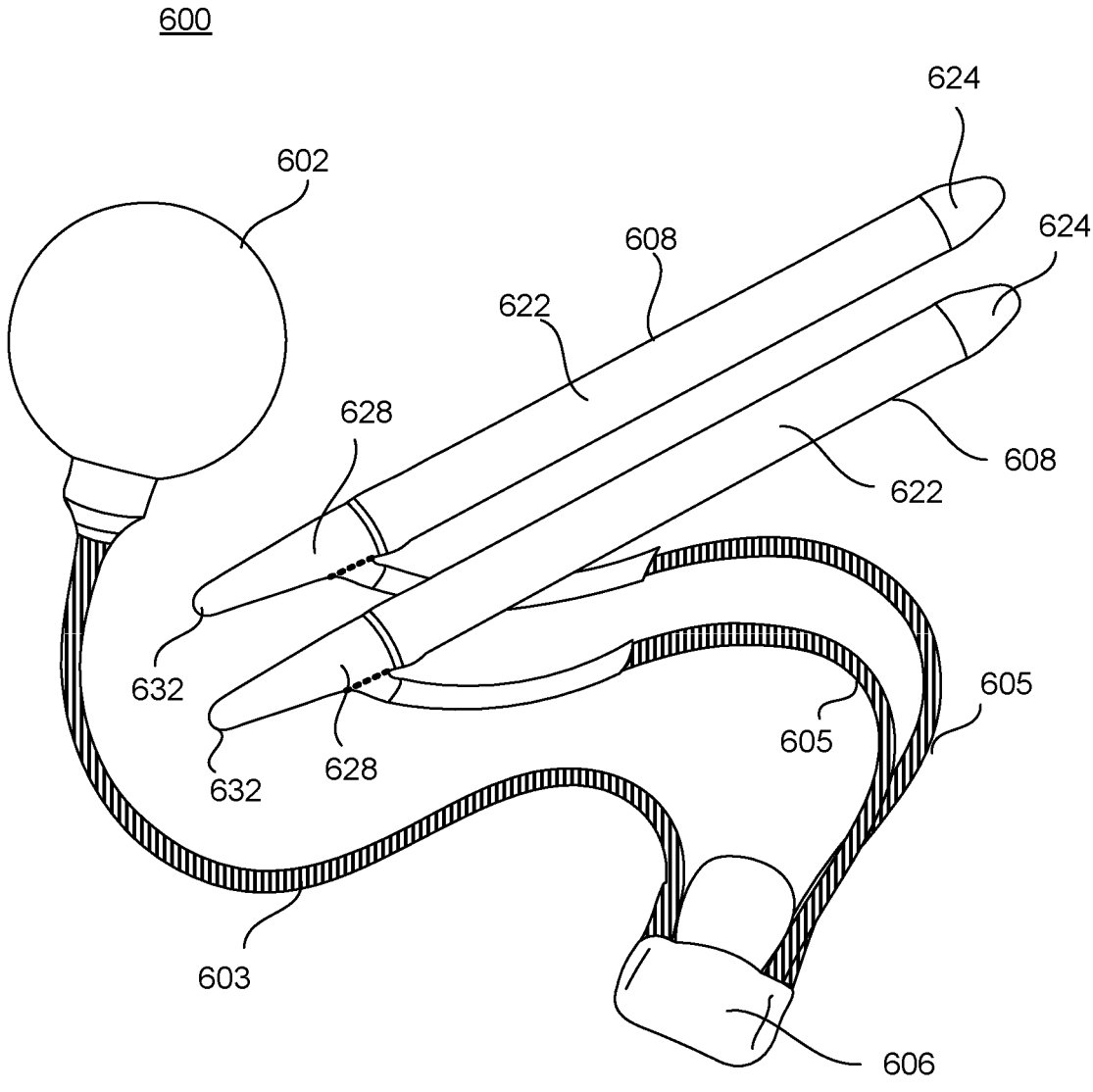
FIG. 6 illustrates an inflatable penile prosthesis according to an aspect.

FIG. 6 illustrates an inflatable penile prosthesis 600 according to an aspect. The inflatable penile prosthesis 600 may be an example of any of the implantable devices discussed herein, and may include any of the features discussed with reference to the previous figures. The inflatable penile prosthesis 600 includes a pump assembly 606. The pump assembly 606 may be the pump assembly 106 of FIG. 1, the pump assembly 206 of FIG. 2, the pump assembly 306 of FIG. 3, or the pump assembly 406 of FIG. 4.

The penile prosthesis 600 may include a pair of cylinders 608, and the pair of cylinders or inflatable members 608 are configured to be implanted in a penis. For example, one of the cylinders 608 may be disposed on one side of the penis, and the other cylinder 608 of the pair of cylinders may be disposed on the other side of the penis. The cylinder 608 may include a first end portion 624, a cavity or inflation chamber 622, and a second end portion 628 having a rear tip 632.

The pump assembly 606 may be implanted into the patient's scrotum. A pair of conduit connectors 605 may attach the pump assembly 606 to the pair of inflatable members or cylinders 608 such that the pump assembly 606 is in fluid communication with the pair of inflatable members or cylinders 608. Also, the pump assembly 606 may be in fluid communication with the fluid reservoir 602 via a conduit connector 603. The fluid reservoir 602 may be implanted into the user's abdomen. The inflation chamber or portion 622 of the cylinder 608 may be disposed within the penis. The first end portion 624 of the cylinder 608 may be at least partially disposed within the crown portion of the penis. The second end portion 628 may be implanted into the patient's pubic region PR with the rear tip 632 proximate the pubic bone PB.

In order to implant the inflatable members or cylinders 608, the surgeon first prepares the patient. The surgeon often makes an incision in the penoscrotal region, e.g., where the base of the penis meets with the top of the scrotum. From the penoscrotal incision, the surgeon may dilate the patient's corpus cavernosae to prepare the patient to receive the pair of inflatable members or cylinders 608. The corpus cavernosum is one of two parallel columns of erectile tissue forming the dorsal part of the body of the penis, e.g., two slender columns that extend substantially the length of the penis. The surgeon will also dilate two regions of the pubic area to prepare the patient to receive the second end portion 628. The surgeon may measure the length of the corpora cavernosae from the incision and the dilated region of the pubic area to determine an appropriate size of the inflatable members or cylinders 608 to implant.

After the patient is prepared, the penile prosthesis 600 is implanted into the patient. The tip of the first end portion 624 of each cylinder 608 may be attached to a suture. The other end of the suture may be attached to a needle member (e.g., Keith needle). The needle member is inserted into the incision and into the dilated corpus cavernosum. The needle member is then forced through the crown of the penis. The surgeon tugs on the suture to pull the cylinder 608 into the corpus cavernosum. This is done for each cylinder of the pair of cylinders 608. Once the inflation chamber 622 is in place, the surgeon may remove the suture from the tip. The surgeon then inserts the second end portion 628. The surgeon inserts the rear end of the cylinder 608 into the incision and forces the second end portion 628 toward the pubic bone PB until each cylinder 608 is in place.

The patient may operate the pump assembly 606 to start an inflation mode, where one or more of the electronically powered pumps of the pump assembly 606 are configured to facilitate the transfer of fluid from the fluid reservoir 602 to the cylinders 608. In some examples, when the user switches to the deflation mode, at least some of the fluid can automatically be transferred back to the fluid reservoir 602 (due to the difference in pressure from the cylinders 608 to the fluid reservoir 602). In some examples, one or more of the electronically powered pumps of the pump assembly 606 may facilitate the transfer of fluid from the cylinders 608 to the fluid reservoir 602.

Figure 7:
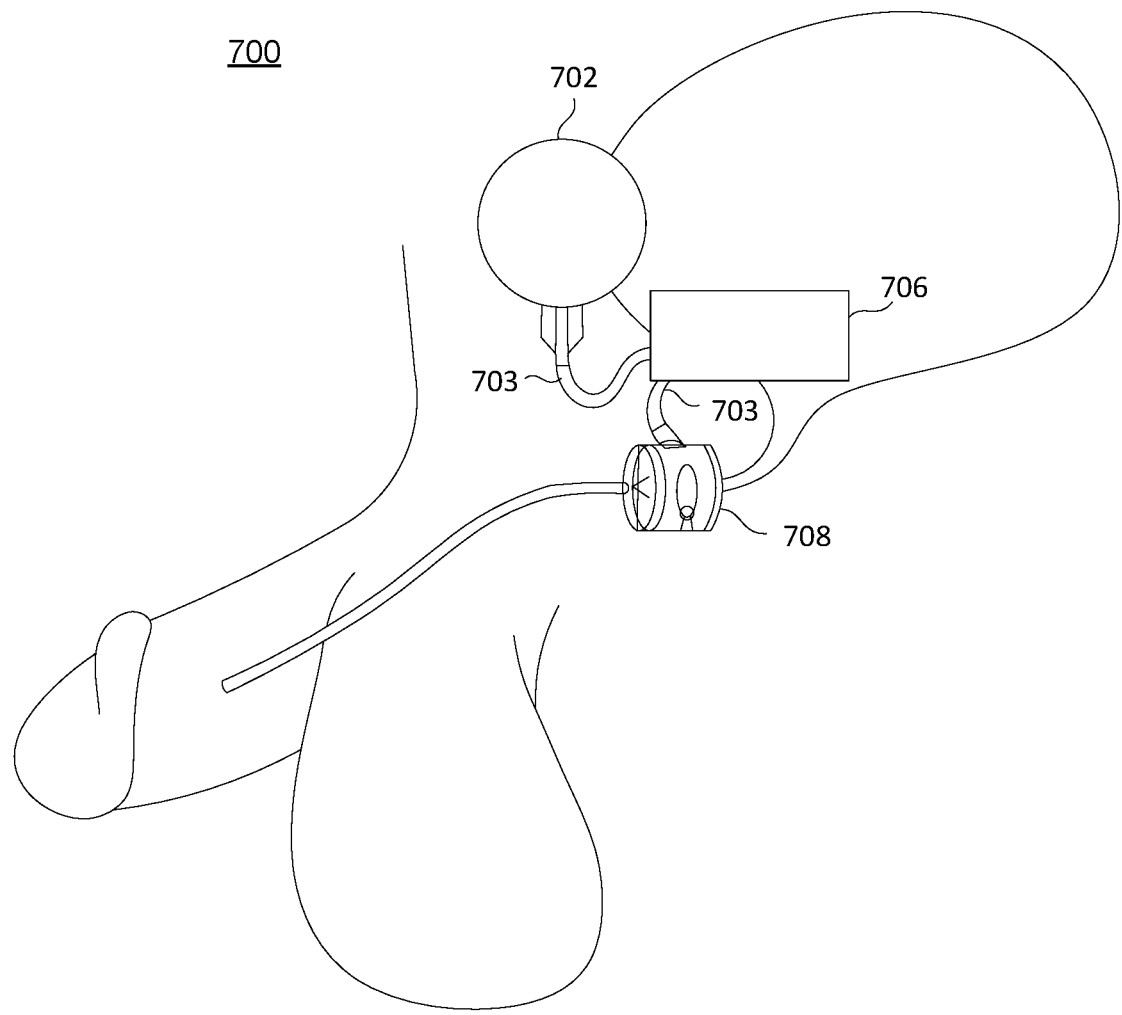
FIG. 7 illustrates a urinary control device according to an aspect.

FIG. 7 illustrates a urinary control device 700 according to an aspect. The urinary control device 700 may be an example of any of the implantable devices discussed herein, and may include any of the features discussed with references to FIGS. 1 through 5. The urinary control device 700 includes a pump assembly 706, a fluid reservoir 702, and a cuff 708. The pump assembly 706 may be the pump assembly 106 of FIG. 1, the pump assembly 206 of FIG. 2, the pump assembly 306 of FIG. 3, or the pump assembly 406 of FIG. 4.

The fluid reservoir 702 may be a pressure-regulating inflation balloon or element. The fluid reservoir 702 is in operative fluid communication with the cuff 708 via one or more tube members 703, chambers, valves or similar structures. The fluid reservoir 702 is constructed of polymer material that is capable of elastic deformation to reduce fluid volume within the fluid reservoir 702 and push fluid out of the fluid reservoir 702 and into the cuff 708. However, the material of the fluid reservoir 702 can be biased or include a shape memory construct adapted to generally maintain the fluid reservoir 702 in its expanded state with a relatively constant fluid volume and pressure. In some examples, this constant level of pressure exerted from the fluid reservoir 702 to the cuff 708 will keep the cuff 708 at a desired inflated state when open fluid communication is provided between the fluid reservoir 702 and the cuff 708. This is largely due to the fact that only a small level of fluid displacement is required to inflate or deflate the cuff 708. In some examples, the fluid reservoir 702 is implanted into the abdominal space.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:
1. An implantable device comprising:
   a fluid reservoir configured to hold fluid, the fluid reservoir configured to be implanted in a body of a patient at a first location;
   an inflatable member configured to be implanted in the body of the patient at a second location;
   a pump assembly configured to be implanted in the body of the patient at a third location, the pump assembly configured to transfer the fluid from the fluid reservoir to the inflatable member via a first fluidic pathway in response to the implantable device being in an inflation mode, the pump assembly configured to transfer the fluid from the inflatable member to the fluid reservoir via a second fluidic pathway different than the first fluidic pathway in response to the implantable device being in a deflation mode,
   the pump assembly including an electronic control module, an electronically powered pump disposed within the first fluidic pathway, a single valve disposed within the first fluidic pathway, an electronically powered pump disposed within the second fluidic pathway, and a single valve disposed within the second fluidic pathway, the electronic control module configured to activate or deactivate the electronically powered pump disposed within the first fluidic pathway, the electronic control module configured to activate or deactivate the electronically powered pump disposed within the second fluidic pathway;
   a first pressure sensor configured to monitor a pressure of the inflatable member; and
   a second pressure sensor configured to monitor a pressure of the fluid reservoir.
2. The implantable device of claim 1, wherein,
   the first pressure sensor is communicatively coupled to the electronic control module, the electronic control module is configured to deactivate the electronically powered pump disposed within the first fluidic pathway in response to the pressure of the inflatable member exceeding a threshold level.
3. The implantable device of claim 1, wherein the valve disposed within the first fluidic pathway is an active valve configured to be electronically controlled.

4. The implantable device of claim 1, wherein the valve disposed within the first fluidic pathway is a passive one-way valve.

5. The implantable device of claim 1, wherein the valve disposed within the second fluidic pathway is an active valve configured to be electronically controlled.

6. The implantable device of claim 1, wherein the valve disposed within the second fluidic pathway is a passive one-way valve.

7. The implantable device of claim 1, wherein the inflatable member is a pair of inflatable cylinders configured to be implanted in a corpora cavernosa of the patient.

8. The implantable device of claim 1, wherein the inflatable member is an inflatable cuff configured to be placed around a urethra of the patient.

9. The implantable device of claim 1, wherein the first pressure sensor is disposed fluidically between the pump assembly and the inflatable member, the second pressure sensor is disposed fluidically between the pump assembly and the fluid reservoir.

10. An implantable device comprising:

a fluid reservoir configured to hold fluid, the fluid reservoir configured to be implanted in a body of a patient at a first location;

an inflatable member configured to be implanted in the body of the patient at a second location;

a pump assembly configured to be implanted in the body of the patient at a third location, the pump assembly configured to transfer the fluid from the fluid reservoir to the inflatable member via a first fluidic pathway in response to the implantable device being in an inflation mode, the pump assembly configured to transfer the fluid from the inflatable member to the fluid reservoir via a second fluidic pathway different than the first fluidic pathway in response to the implantable device being in a deflation mode, the pump assembly including an electronic control module, an electronically powered pump disposed within the first fluidic pathway, a single valve disposed within the first fluidic pathway, an electronically powered pump disposed within the second fluidic pathway, a single valve disposed within the second fluidic pathway, and an interface element, the electronic control module configured to activate the electronically powered pump disposed within the first fluidic pathway in response to activation of the interface element by the patient;

a first pressure sensor configured to monitor a pressure of the inflatable member; and a second pressure sensor configured to monitor a pressure of the fluid reservoir.

11. The implantable device of claim 10, wherein, the first pressure sensor being communicatively coupled to the electronic control module, the electronic control module configured to deactivate the electronically powered pump disposed within the first fluidic pathway in response to the pressure of the inflatable member exceeding a threshold level.

12. The implantable device of claim 10, wherein the first pressure sensor is disposed fluidically between the pump assembly and the inflatable member, the second pressure sensor is disposed fluidically between the pump assembly and the fluid reservoir.

* * * * *